(12) United States Patent
Sakamoto (10) Patent No.: US 7,510,523 B2
(45) Date of Patent: Mar. 31, 2009

(54) METHOD FOR FIXING ONE OF BALLOON AND TUBULAR MEMBER, AND MEDICAL EQUIPMENT

(75) Inventor: Toshio Sakamoto, Saitama (JP)

(73) Assignee: Fujinon Corporation, Saitama (JP)

( * ) Notice: Subject to any disclaimer, the term of this patent is extended or adjusted under 35 U.S.C. 154(b) by 750 days.

(21) Appl. No.: 11/012,248

(22) Filed: Dec. 16, 2004

(65) Prior Publication Data
US 2005/0137458 A1 Jun. 23, 2005

(30) Foreign Application Priority Data

| Dec. 17, 2003 | (JP) | 2003-419810 |
| Dec. 17, 2003 | (JP) | 2003-419811 |
| Nov. 4, 2004 | (JP) | 2004-321222 |
| Nov. 4, 2004 | (JP) | 2004-321223 |

(51) Int. Cl.
*A61B 1/00* (2006.01)
(52) U.S. Cl. ............... 600/116; 600/115; 604/103; 604/96.01; 604/921; 140/93.4; 57/213; 156/144
(58) Field of Classification Search ......... 600/115–116; 604/96.01, 103; 156/144
See application file for complete search history.

(56) References Cited

U.S. PATENT DOCUMENTS

| 3,746,003 A | * | 7/1973 | Blake et al. ......... 604/102.02 |
| 5,100,386 A | * | 3/1992 | Inoue .................... 604/103 |
| 5,334,210 A | * | 8/1994 | Gianturco ............... 606/151 |
| 5,549,552 A | * | 8/1996 | Peters et al. ........... 604/103.1 |
| 5,578,010 A | * | 11/1996 | Ashby .................. 604/96.01 |
| 5,868,704 A | * | 2/1999 | Campbell et al. ....... 604/103.11 |
| 6,002,551 A | * | 12/1999 | Goss et al. .............. 360/264.2 |
| 6,536,483 B2 | * | 3/2003 | Zettel et al. ............. 140/71 R |
| 7,331,933 B2 | * | 2/2008 | Steadham et al. ....... 604/96.01 |
| 2007/0083132 A1 | * | 4/2007 | Sharrow ................ 600/585 |

FOREIGN PATENT DOCUMENTS

| FR | 2 716 114 A | 8/1995 |
| JP | 62-246358 | 10/1987 |
| JP | 2001-152440 | 6/2001 |
| JP | 2003-235847 | 8/2003 |

OTHER PUBLICATIONS

Office Action mailed Feb. 3, 2006 for corresponding Japanese application and English translation thereof.
European Search Report dated Apr. 25, 2005.
Abstract of JP 2003 235847-A dated Aug. 26, 2003.
Abstract of JP 10216133-A dated Aug. 18, 1998.
Abstract of JP 01254172 dated Oct. 11, 1989.
Abstract of JP 2001 340462 dated Dec. 11, 2001.

* cited by examiner

*Primary Examiner*—Linda C Dvorak
*Assistant Examiner*—Matthew J Kasztejna
(74) *Attorney, Agent, or Firm*—Harness, Dickey & Pierce PLC

(57) ABSTRACT

A method for fixing one of a balloon and a tubular member to an object with a thread for a medical equipment, may include covering the object with an end of the one of the balloon and the tubular member, winding the thread at a first pitch in a first direction from an edge of the end of the one of the balloon and the tubular member toward an intermediate position of the one of the balloon and the tubular member, and winding the thread at a second pitch in a second direction opposite to the first direction, the second pitch being shorter than the first pitch.

17 Claims, 10 Drawing Sheets

RELATED ART

METHOD FOR FIXING ONE OF BALLOON AND TUBULAR MEMBER, AND MEDICAL EQUIPMENT

BACKGROUND OF THE INVENTION

1. Field of the Invention

The present invention relates to a method for fixing one of a balloon and a tubular member, and more particularly, to a method for fixing one of a balloon and a tubular member, which fixes an end of the tubular member by winding a thread and medical equipment with a tubular member, fixed using this method.

2. Description of the Related Art

In an endoscopic apparatus, a balloon that can expand or shrink is used for various purposes. For example, an ultrasonograph comprises a balloon surrounding an ultrasonic scanning section at an end of an ultrasonic probe to charge an ultrasonic transmission medium thereinto, and an ultrasonic endoscope comprises a balloon surrounding an ultrasonic transducer at an end of the insertion section to charge an ultrasonic transmission medium thereinto. Furthermore, a balloon is attached to an insertion section of an endoscope to fix the insertion section or a balloon is attached to an insertion adapter such as an over tube to fix the insertion adapter inside a body cavity.

In the case of such a balloon for a medical equipment, an end of the balloon is put on an object and fixed with a thread wound around the end of the balloon. For example, in the ultrasonic detection apparatus as described in Japanese Patent Application Publication No. 2003-235847, the end of a balloon is covered on a ring, a thread is wound around the balloon, and adhesive is applied further thereon, so that the balloon is fixed on the ring.

However, the method of winding or knotting a thread is not described specifically in Japanese Patent Application Publication No. 2003-235847. For this reason, since a fastening force is weakened depending on the method of winding or knotting a thread, the balloon may come off or the mounting position of the balloon may be deviated, so that an adverse effect on an inspection using ultrasound may be caused.

Figure 6A:
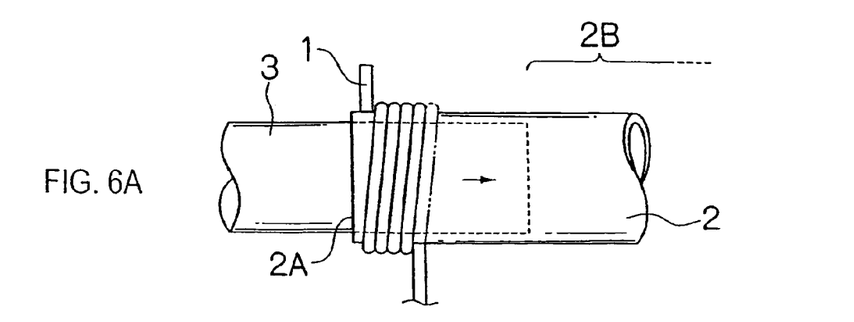
FIGS. 6A to 6D are perspective side views showing a conventional fixing method.

For example, as shown in FIG. 6A, a balloon 2 is put on an object 3 such as a ring, and a thread 1 is wound densely around the balloon 2 from an edge 2A thereof. Therefore, the balloon 2 is pressed by the thread 1 and stretches in the direction indicated by an arrow, which results in a disadvantage that the size of the expanded area (i.e., area expanded or shrunken by a supply or suction of a fluid) 2B of the balloon 2 changes. For this reason, when an ultrasonic transducer is disposed inside the balloon 2, the positional relationship between the ultrasonic transducer and the maximum expanded area of the balloon 2 may be shifted, making it hard for ultrasound to propagate and causing an adverse effect on measurement.

Figure 6B:
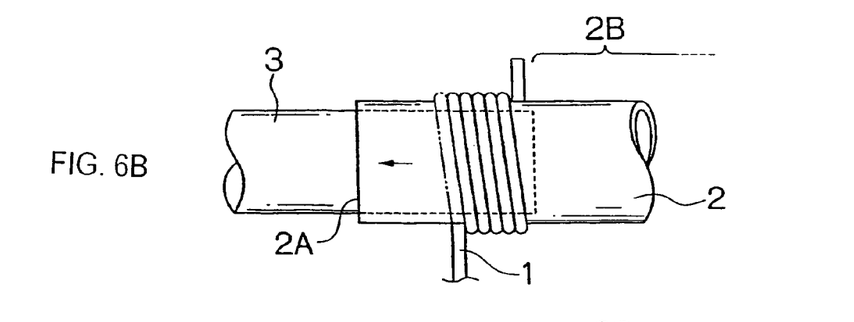

Such a problem can be solved by densely winding the thread 1 toward the edge 2A of the balloon 2 as shown in FIG. 6B. However, in this case, a new problem occurs depending on how the thread 1 is tied after winding.

Figure 6C:
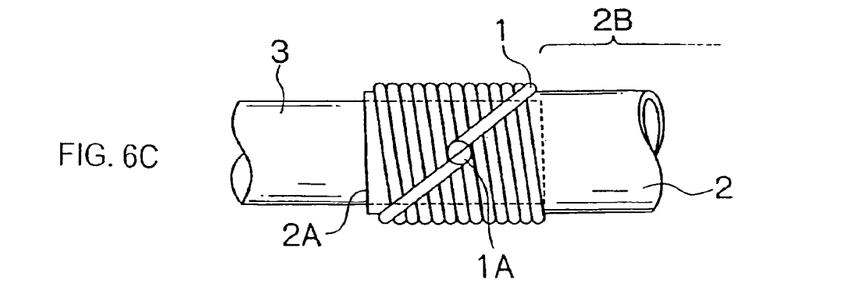

For example, as shown in FIG. 6C, a method of tying the ends of the thread 1 together on the winding portion has a disadvantage that slackens the tying thread 1 easily, and a disadvantage that snags a jutting knot 1A of the thread 1 from rest of the part easily.

Figure 6D:
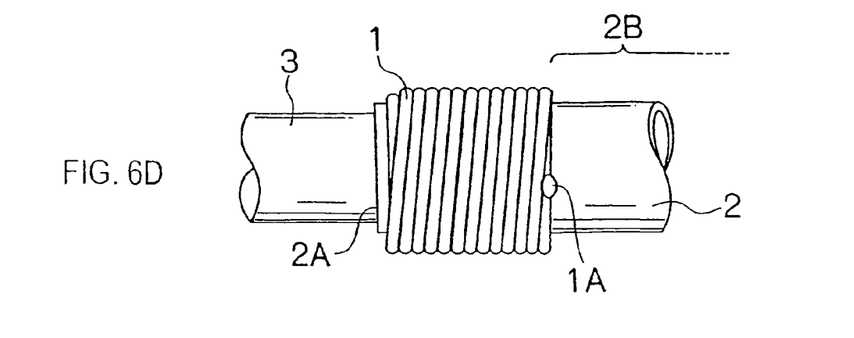

Furthermore, as shown in FIG. 6D, it is possible to consider a method of densely winding the thread 1 toward the edge 2A of the balloon 2 first and then winding the thread 1 from the edge 2A, thus winding twofold. However, this method has a problem that the twofold-winding thread 1 causes to increase the diameter of the winding part. Another problem is that the inner thread 1 is likely to slacken when the outer thread 1 is wound. In addition, since the thread 1 is tied in the vicinity of the expanded area 2B of the balloon 2, the knot 1A of the thread 1 may tear the balloon 2 when the balloon 2 is expanded or shrunken.

Therefore, depending on how the thread 1 is wound or tied, the balloon 2 would conventionally result in various problems such as the balloon 2 getting expanded or damaged or the diameter of the winding part of the thread 1 becoming large. Such problems also occur when the balloon is attached to an insertion adapter or endoscope operating equipment or when an angle rubber, etc., to cover the insertion section of the endoscope is fixed.

Additionally, Japanese Patent Application Publication No. 2003-235847 does not specifically describe how to wind or tie the thread, and therefore the knot of the thread may protrude from the rest of the part. When the ultrasonograph with the protrusion is inserted into a clamp channel of the endoscope, the protrusion may be caught at the knot of the thread, tearing the balloon. Such problems may also occur when the balloon is fixed to the insertion adapter and endoscope operating equipment, or when the angle rubber and the like for covering the insertion section of the endoscope are fixed to those.

SUMMARY OF THE INVENTION

The present invention is contrived in view of such circumstances, and an object thereof is to provide a method for fixing one of a balloon and a tubular member that can fix reliably one of a balloon and a tubular member such as angle rubber used to a medical equipment without damaging thereto and without increasing the diameter thereof, and also to provide a medical equipment comprising one of the balloon and the tubular member fixed by this method.

Furthermore, another object of the present invention is to provide a method for fixing one of a balloon and a tubular member used to a medical equipment without forming any protrusion, and also to provide a medical equipment comprising one of the balloon and the tubular member fixed by this method.

In order to attain the above described object, a first aspect of the invention is a method for fixing one of a balloon and a tubular member to an object with a thread for a medical equipment, comprising the steps of: covering the object with an end of the one of the balloon and the tubular member; then winding the thread at a first pitch in a first direction from an edge of the end of the one of the balloon and the tubular member toward an intermediate position of the one of the balloon and the tubular member; and then winding the thread at a second pitch in a second direction opposite to the first direction, the second pitch being shorter than the first pitch.

According to the first aspect of the invention, since first the thread is wound roughly at the first pitch, it is possible to prevent one of the balloon and the tubular member from stretching by the thread.

In addition, the thread is wound roughly at the first pitch in the first direction (i.e., the direction from the edge of the end of one of the balloon and a tubular member toward an intermediate position of one of the balloon and a tubular member), and then the thread is wound densely at the second pitch in the second direction opposite to the first direction. In this case, since the second pitch is different length from the first pitch, the thread is hard to slacken when the thread is wound densely at the second pitch. Therefore, it is possible to fix one of the balloon and the tubular member to the object firmly. Furthermore, since the thread is wound densely on the thread which has been wound roughly, it is possible to reduce the diameter compared to the case where the thread is wound densely twofold.

Moreover, since the thread wound in the first direction is wound in the second direction opposite to the first direction (i.e., the direction from the intermediate position of one of the balloon and a tubular member toward the edge of the end of one of the balloon and a tubular member), both ends of the thread after winding are disposed on the edge side of one of the balloon and the tubular member. Therefore, the knot of the thread is disposed on the edge side (i.e., opposite to the intermediate section), which prevents one of the balloon and the tubular member from being damaged by the knot of the thread.

A second aspect of the invention is the method for fixing one of a balloon and a tubular member in the first aspect, wherein the object is one of an insertion section of an endoscope, an insertion adapter covered over the insertion section for assisting in inserting the insertion section, and an endoscope operating equipment for inserting through a clamp channel of the endoscope.

In order to attain the above described object, a third aspect of the invention is a medical equipment, comprising: an endoscope insertion section provided a clamp channel; an insertion adapter for assisting in inserting the endoscope insertion section; a long-length medical operating equipment inserted through the clamp channel or directly into a body cavity; and one of a balloon and a tubular member fixed with a thread to the medical operating equipment, wherein: the thread is wound at a first pitch in a first direction from an edge of the end of the one of the balloon and the tubular member toward an intermediate position of the one of the balloon and the tubular member; and then the thread is wound at a second pitch in a second direction opposite to the first direction, the second pitch being shorter than the first pitch.

In order to attain the above described object, a fourth aspect of the invention is a method for fixing one of a balloon and a tubular member to an object with a thread for a medical equipment, comprising the steps of: covering the object with the one of the balloon and the tubular member; then winding a thread around the one of the balloon and the tubular member; and then knotting both ends of the thread on the object.

According to the fourth aspect of the present invention, since the knot of the thread is positioned on the object, it is possible to prevent any protrusion from being formed by the knot of the thread as in the case where the knot of the thread is positioned on the tubular member.

In order to attain the above described object, a fifth aspect of the present invention is a method for fixing one of a balloon and a tubular member to an object with a thread for a medical equipment, comprising the steps of: covering the object with the one of the balloon and the tubular member; then winding the thread around an end of the one of the balloon and the tubular member; and then fusing both ends of the thread so as to fix.

According to the fifth aspect of the present invention, since both ends of the thread are fixed by fusing, it is possible to prevent any protrusion from being formed. In addition, since only the both ends are fused, it is possible to prevent the thread from slackening by fusing the entire thread. Therefore, according to the fifth aspect of the present invention, one of the balloon and the tubular member can be fixed reliably without forming any protrusion.

A sixth aspect of the present invention is the method for fixing one of a balloon and a tubular member in a fifth aspect, wherein the both ends of the thread is fused on the object.

According to the sixth aspect, since the fused part of the thread is positioned on the object, it is possible to prevent any protrusion from being formed reliably by positioning the fused part of the thread on the balloon or tubular member.

Each of seventh to ninth aspects of the present invention is each of the fourth to sixth aspects, wherein the object is one of an insertion section of an endoscope, an insertion adapter covered over the insertion section for assisting in inserting the insertion section, and an endoscope operating equipment for inserting through a clamp channel of the endoscope.

In order to attain the above described object, an tenth aspect of the present invention is a medical equipment, comprising: a long-length insertion section for inserting into a body cavity; one of a balloon and a tubular member fixed on the insertion section; and a thread for fixing the one of a balloon and a tubular member to the insertion section by being wound, wherein: both ends of the thread are knotting on the insertion section neighborhood the end of one of the balloon and the tubular member.

An eleventh aspect of the present invention is the medical equipment in a tenth aspect, wherein the both ends of the thread are fused so as to fix.

According to the method for fixing one of a balloon and a tubular member of the present invention, a thread is wound roughly at the first pitch in the first direction, and then is wound densely at the second pitch which is shorter than the first pitch, in the second direction opposite to the first direction. Therefore, it is possible to reliably fix the balloon or the tubular member without causing problems such as damage to the balloon or the tubular member, or without causing problems such as increase in the diameter of the object. Furthermore, according to the medical equipment of the present invention, the balloon or the tubular member is attached with the insertion section by winding the thread densely at the second pitch in the second direction after winding the thread roughly at the first pitch in the first direction opposite to the second direction. Therefore, it is possible to prevent the tubular member from being damaged and to prevent the diameter of the fixed part from increasing.

Moreover, according to the method for fixing a tubular member of the present invention, since the knot of the thread is positioned on the object while fusing the both ends of the thread, it is possible to tie the threads together without forming any protrusion. Furthermore, according to the medical equipment of the present invention, the knot of the thread is positioned on the object, or/and, both ends of the thread are fused, so it is possible to reduce the diameter without forming any protrusion.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Figure 1:
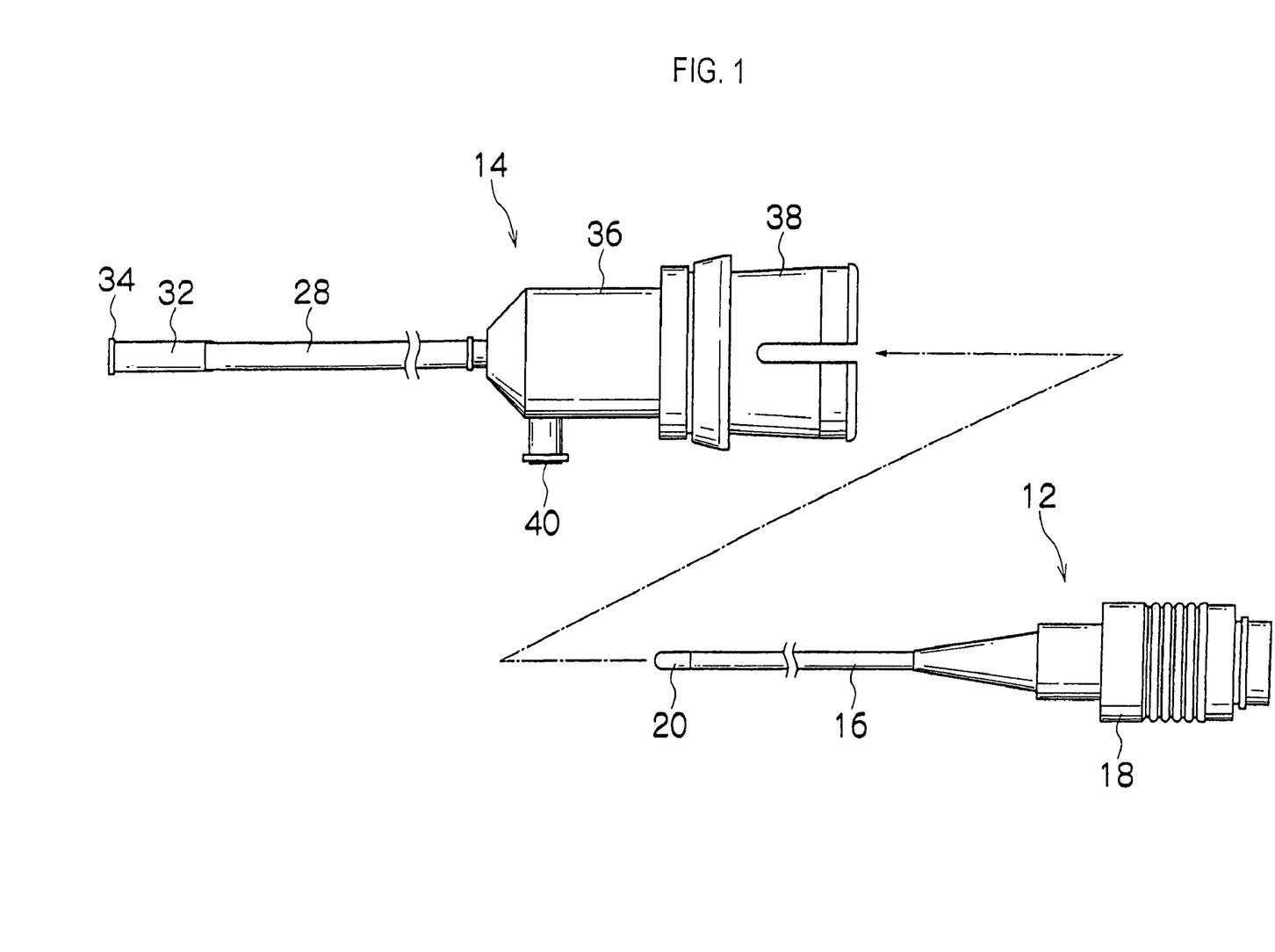
FIG. 1 is a system block diagram of an ultrasonograph according to an embodiment of the present invention.

FIG. 1 is a system block diagram of an ultrasonograph according to an embodiment of the present invention. As shown in FIG. 1, the ultrasonograph is mainly composed of an ultrasound probe 12 and a balloon apparatus 14.

Figure 2:
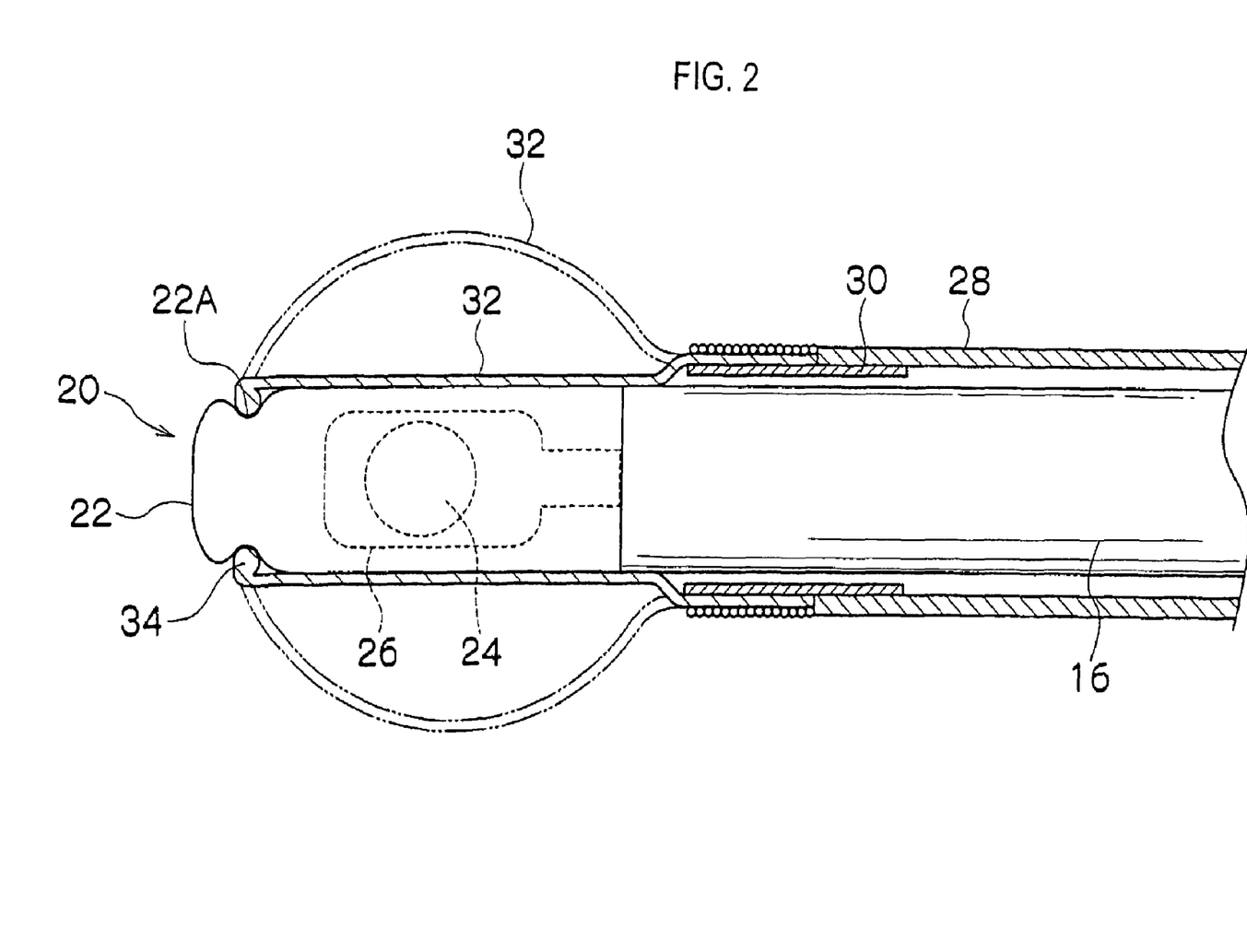
FIG. 2 is a cross-sectional view showing an end of the ultrasonograph.

The ultrasound probe 12 comprises: a flexible cord 16; a connector 18 provided at a base end of this flexible cord 16; and an ultrasonic scanning section 20 provided at an end of the flexible cord 16. As shown in FIG. 2, the ultrasonic scanning section 20 is provided with an end cap 22, and an ultrasonic transducer 24 is provided inside the end cap 22. The ultrasonic transducer 24 is mounted on a rotary mount 26, and the rotary mount 26 is connected to a flexible shaft inside the flexible cord 16. A ring-shaped concave groove 22A is formed on the outer surface at the end of the end cap 22.

On the other hand, as shown in FIG. 1, the balloon apparatus 14 comprises: a flexible tube 28; a mounting ring 30 attached at the end of this flexible tube 28; and a thin-film cylindrical balloon 32 attached to the mounting ring 30. The balloon 32 is fixed to the flexible tube 28 by a fixing method as described later, and an elastic ring 34 is attached at the end thereof. A holding cylinder 36 in FIG. 1 is connected to the base end of the flexible tube 28 and a fastening ring 38 is attached to this holding cylinder 36.

The aforementioned ultrasound probe 12 is inserted from the base end side of the balloon apparatus 14, and is fixed to the balloon apparatus 14 by fastening the connector 18 on the holding cylinder 36 with the fastening ring 38. In this case, the elastic ring 34 shown in FIG. 2 fits into the concave groove 22A of the ultrasonic scanning section 20, and the ultrasonic scanning section 20 is covered with the balloon 32. By supplying an ultrasonic transmission medium (for example, deaerated water) through a supply port 40 of the holding cylinder 36 in FIG. 1, the interior of the balloon 32 is filled with the ultrasonic transmission medium. Therefore, the ultrasound can be transmitted and received efficiently by the ultrasonic transducer 24, so that the measurement using ultrasound can be performed accurately.

Next, the method for fixing the balloon 32 described above is explained.

Figure 3A:
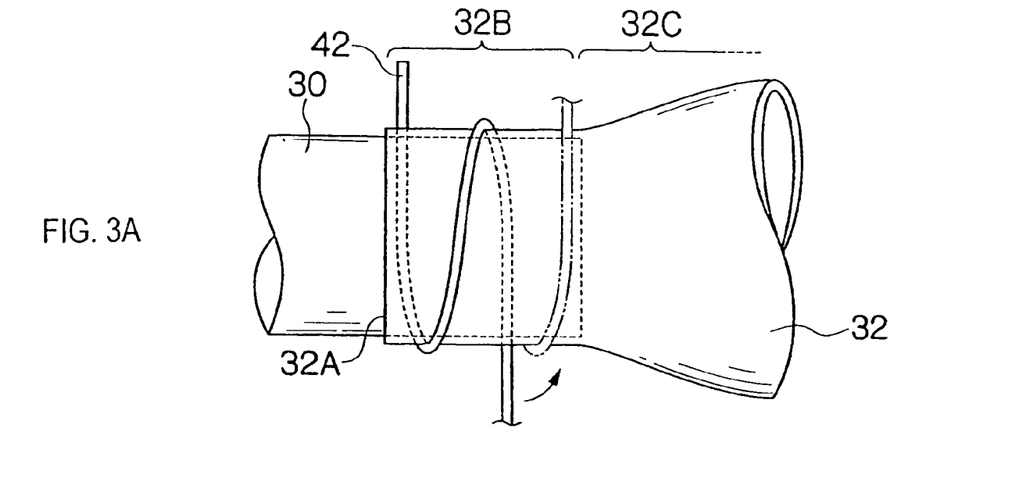
FIGS. 3A to 3C are perspective side views showing a method for fixing the balloon according to an embodiment.

As shown in FIG. 3A, a thread 42 is wound roughly from an edge 32A of the balloon 32. The "winding roughly" means the first pitch of winding the thread 42 spirally so as to create clearance between neighboring parts of the thread 42. For example, in the case that the diameter of the thread 42 is approximately 0.1 mm or less and the length 32B of the fixed part of the balloon 32 (area wound with the thread 42) is approximately 10 mm, it is preferable that the thread 42 is wound by approximately 1 to 3 rolls. Since the thread 42 is wound roughly in this way, it is possible to prevent the balloon 32 from stretching toward an expanded area (area which expands/shrinks because of a supply or suction of a fluid) 32C even if the thread 42 is wound from the edge 32A. Therefore, it is possible to prevent the length of the expanded area 32C of the balloon 32 from changing.

Figure 3B:
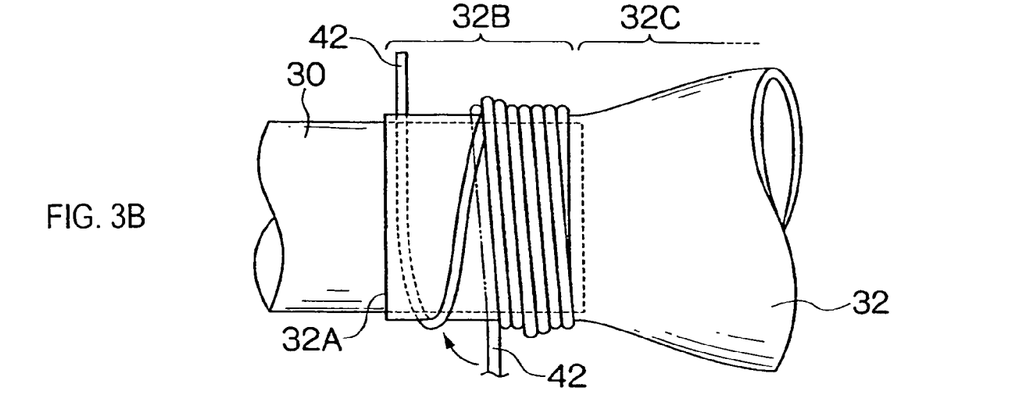

After the thread 42 is wound roughly around the fixed part 32B, the thread 42 is then wound densely toward the edge 32A as shown in FIG. 3B. The "winding densely" means the second pitch of winding the thread 42 at shorter pitch than the first pitch as "winding roughly". In other words, the "winding densely" in this embodiment is to create no clearance between neighboring parts of the thread 42. Therefore, the balloon 32 is fixed to the mounting ring 30 with the thread 42 wound densely. At that time, since the inner thread (i.e., thread wound roughly from the edge 32A) 42 and the outer thread (i.e., thread wound densely toward the edge 32A) 42 are wound with different pitches, the inner thread 42 does not slacken when the outer thread 42 is wound. Therefore, it is possible to fix the balloon 32 to the mounting ring 30 firmly. In addition, since the inner thread 42 is wound roughly, it is possible to reduce the diameter of the fixed part 32B compared to the case winding the thread 42 twofold densely.

Figure 3C:
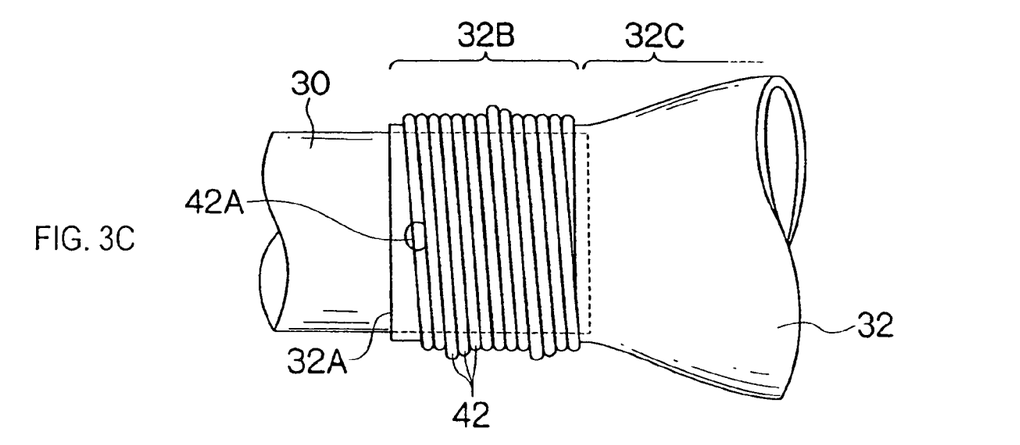

As shown in FIG. 3C, after the thread 42 is wound densely around the fixed part 32B, the both ends of the thread 42 are tied together. Since both ends of the thread 42 are disposed on the edge 32A side in this time, it is possible to tie them together firmly without allowing the thread 42 to slacken. More specifically, in the case that the ends of the thread 42 are disposed separately at both ends of the fixed part 32B, it is difficult to tie those ends together without allowing the thread 42 to slacken. However, in this embodiment, both ends of the thread 42 are disposed on the edge 32A side, it is possible to tie both ends together firmly without slackening the thread 42.

Furthermore, according to the embodiment, since the thread 42 is tied on the edge 32A side (i.e., opposite to the expanded area 32C), it is possible to prevent the expanded area 32C from being damaged when the thread 42 is wound. Moreover, since the knot 42A of the thread 42 is disposed opposite to the expanded area 32C, it is possible to prevent the balloon 32 from being damaged by the knot 42A when the expanded area 32C is expanded or shrunken. The method of tying the ends of the thread 42 together is not limited to tying the ends of the thread 42 together, but the ends of the thread 42 may be bonded using an adhesive or fused by heating the thread 42.

According to the above described embodiment, since the thread 42 is wound densely toward the edge 32A after winding the thread 42 roughly from the edge 32A of the balloon 32 first and the ends of the thread 42 are tied together, it is possible to avoid problems such as a stretch or damage of the balloon 32 and reduce the diameter of the fixed part 32B of the balloon 32.

Although only one end of the balloon 32 is fixed in the above-described embodiment, it is also preferable to fix both ends of the balloon 32. In addition, the balloon 32 is explained as cylindrical form in the embodiment, but the shape of the balloon 32 is not limited to those. The balloon 32 may be formed like a bag (i.e., a shape with only one end left open).

The above-described embodiment is applied to the method for fixing the balloon 32 of the ultrasonograph, but the balloon fixed by the present invention is not limited to an example as described above. Various balloon used for a medical equipment can be fixed by the present invention. For example, the present invention is also adapted in the case in which the balloon of an ultrasonic endoscope is fixed as shown in FIG. 4.

Figure 4:
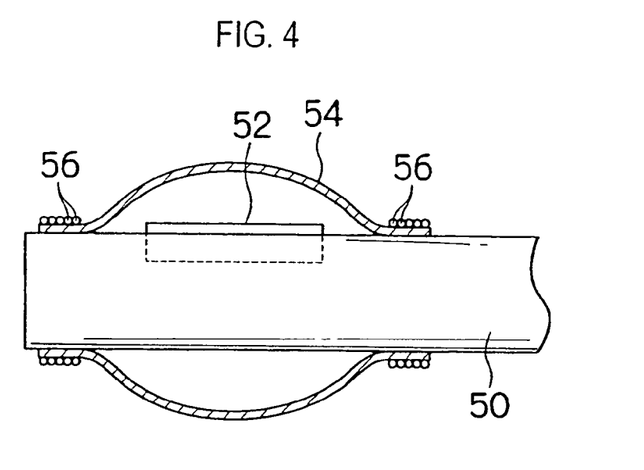
FIG. 4 is a cross-sectional view showing an end of the insertion section of an ultrasonic endoscope according to the embodiment.

As shown in FIG. 4, an ultrasonic transducer 52 is provided on the side of an end of the insertion section 50 of the ultrasonic endoscope. The transducer 52 has a structure in which a plurality of ultrasonic vibrators are arranged along the axial direction on the insertion section 50. A cylindrical balloon 54 is attached to the insertion section 50 at the state of surrounding the transducer 52. The balloon 54 is fixed by winding the thread 56 around both ends thereof. Since the balloon 54 is fixed by the method of the present invention, it is possible to solve problems such as a stretch or damage of the balloon 54 and to reduce the diameter of the fixed part of the balloon 54.

Figure 7:
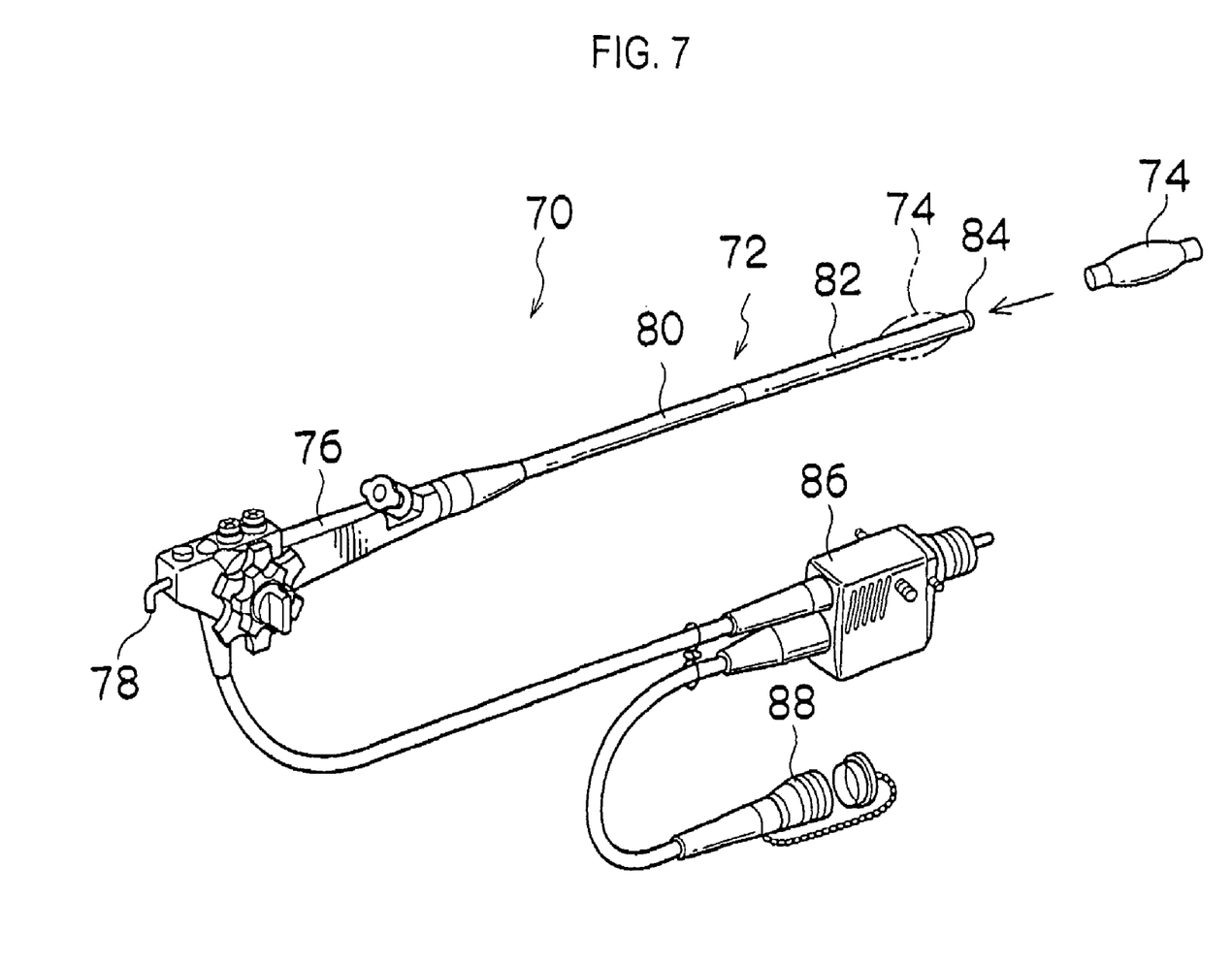
FIG. 7 is a perspective view showing an endoscope according to an embodiment.

As described above, the balloon 32 in FIGS. 2 and 3, and the balloon 54 in FIG. 4 are used for charging an ultrasonic transmission medium (for example, deaerated water), but the method of using the balloon in the present invention is not limited to those. The balloon can be used for other purposes. For example, the balloon 74 may be attached to the outer surface of an insertion section 72 of an endoscope 70 as shown in FIG. 7. Since the balloon 74 expands by supplying a fluid such as air from a supply port 78 of a hand operation section 76, the balloon 74 holds a body cavity such as an intestinal tract, so that the insertion section 72 can be fixed inside the body cavity. When such balloon 74 is fixed by method of the present invention, it can solve problems like stretch or damage of the balloon 74 by the thread. As shown in FIG. 7, the insertion section 72 is composed of a soft section 80, a curved section 82, and an end section 84, respectively. The curvature of the curved section 82 is controlled by operating angle knobs 86 and 86 of the hand operation section 76. Furthermore, an LG connector 86 and an electric connector 88 as shown in FIG. 7 are connected to a light source apparatus (not shown) and a processor (not shown).

Figure 5A:
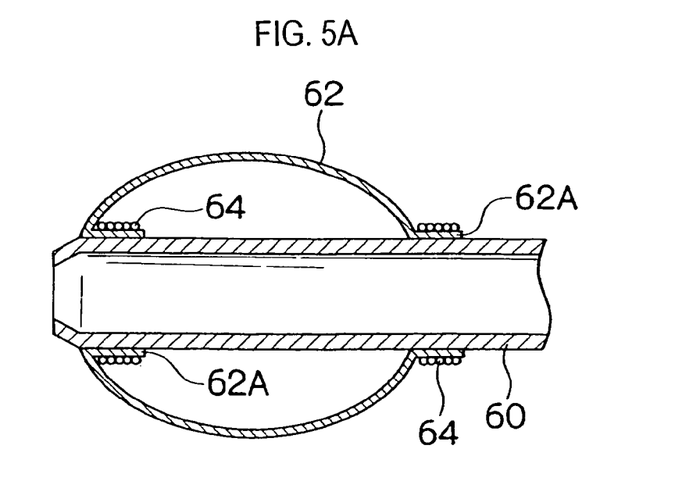
FIGS. 5A and 5B are cross-sectional views showing each ends of the insertion adapter according to of the present invention.

It is preferable that the balloon 74 in FIG. 7 is a balloon 62 for fixing an insertion adapter 60 within a body cavity as shown in FIG. 5A. The balloon 62 is fixed to the end section 82 of the insertion adapter 60 and holds the insertion adapter 60 in the body cavity by supplying a fluid such as air to the balloon 62 so that the balloon 62 is expanded.

Figure 5B:
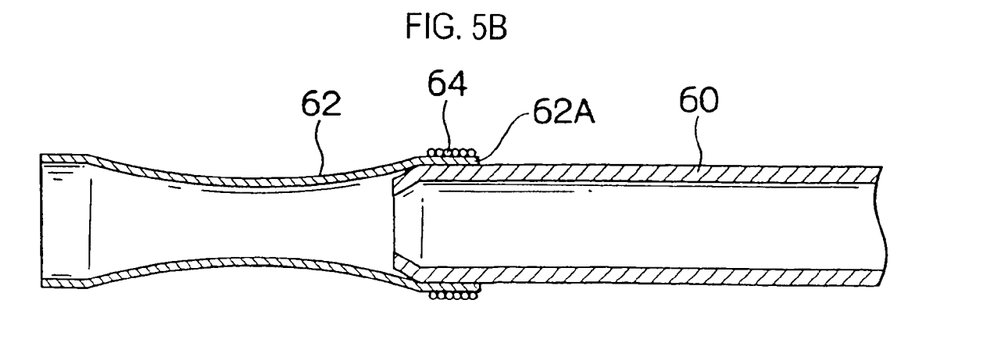

In order to attach the balloon 62 as closely as possible to the end section of the insertion adapter 60, the edge of the balloon 62 may be folded back toward the inside of the balloon 62 to be fixed as shown in FIG. 5A. First, as shown in FIG. 5B, the balloon 62 is turned inside out, and then the turned balloon 62 is fixed to the end section of the insertion adapter 60. Next, after the thread 64 is wound roughly from the edge 62A of the balloon 62, the thread 64 is wound densely toward the edge 62A, and then the ends of the thread 64 are tied together. Therefore, the balloon 62 may be fixed to the insertion adapter 60 firmly without being damaged or stretched. After that, the balloon 62 is turned inside out again (i.e., returned to its original state), and then the other end is fixed likewise. Therefore, the balloon 62 may be fixed without causing problems like stretching or damage of the balloon 62 or increase in the diameter.

The embodiments described above have been explained as examples in which the balloons 32, 54, 62, and 74 are fixed; however, the method for fixing used to the present invention are not limited to those. Any parts having a tubular opening may be adapted to the present invention. For example, it is possible to fix angle rubber, which covers the curved section 82 of the insertion section 72 (referred to FIG. 7) using the method of the present invention. Since the angle rubber is generally made of a material having large elasticity such as rubber, there is a problem that winding a thread may cause deviation of the position of the angle rubber. Therefore, such the problem can be avoided by the present invention.

Next, another embodiment according to the method for fixing the balloon 32 will be explained.

Figure 8A:
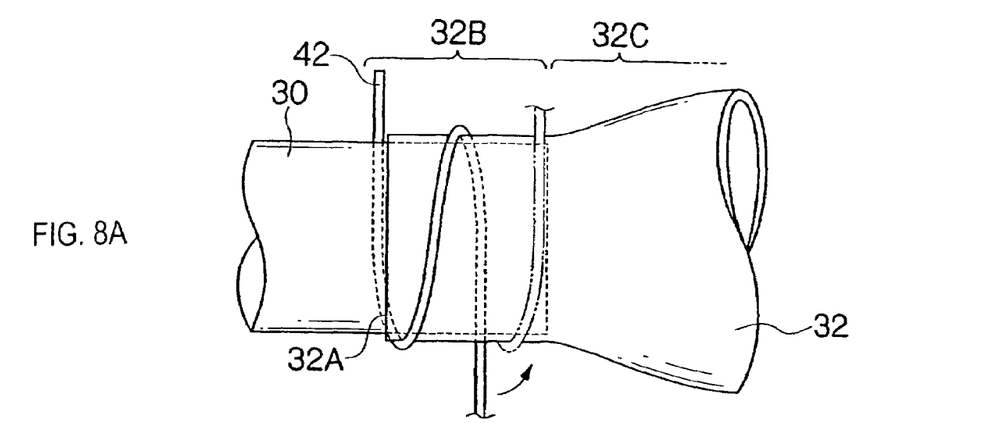
FIGS. 8A to 8C are perspective side views showing a fixing method according to another embodiment.

As shown in FIG. 8A, a thread 42 is wound roughly from the outside of an edge 32A of the balloon 32. The "winding roughly" means winding the thread spirally so that a space is kept between neighboring parts of the thread 42. For example, in the case where the diameter of the thread 42 is approximately 0.1 mm or less while the length 32B of the fixed part of the balloon 32 (area wound with the thread 42) is approximately 10 mm, it is preferable that the thread 42 is wound by approximately 1 to 3 rolls. Since the thread 42 is wound roughly, it is possible to prevent the balloon 32 from stretching toward an expanded area (area which expands/shrinks because of a supply or suction of fluid) 32C even if the thread 42 is wound from the edge 32A. Therefore, it is possible to prevent the length of the expanded area 32C of the balloon 32 from changing.

Figure 8B:
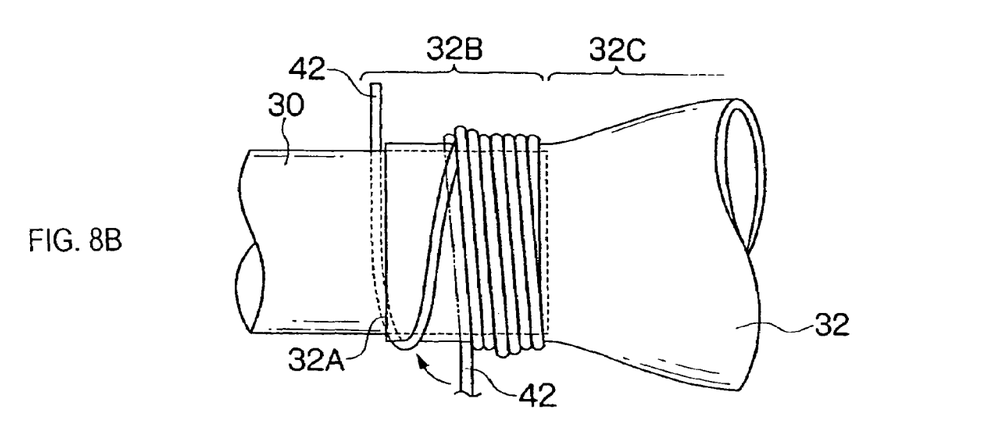

After the thread 42 is wound roughly around the fixed part 32B, the thread 42 is then wound densely toward the edge 32A as shown in FIG. 8B. The "winding densely" means that the pitch between neighboring parts of the thread 42 is smaller than that in the case of the "winding roughly" and in this embodiment. The "winding" in another embodiment is to create no clearance between neighboring parts of the thread 42. Therefore, the balloon 32 is fixed to the mounting ring 30 with the thread 42 wound densely in this way. At that time, since the inner thread (i.e., thread wound roughly from the edge 32A) 42 and the outer thread (i.e., thread wound densely toward the edge 32A) 42 are wound with different pitches, the inner thread 42 does not slacken when the outer thread 42 is wound. Therefore, it is possible to fix the balloon 32 to the mounting ring 30 firmly. In addition, since the inner thread 42 is wound roughly, it is possible to reduce the diameter of the fixed part 32B compared to the case where the thread 42 is wound twofold densely.

Figure 8C:
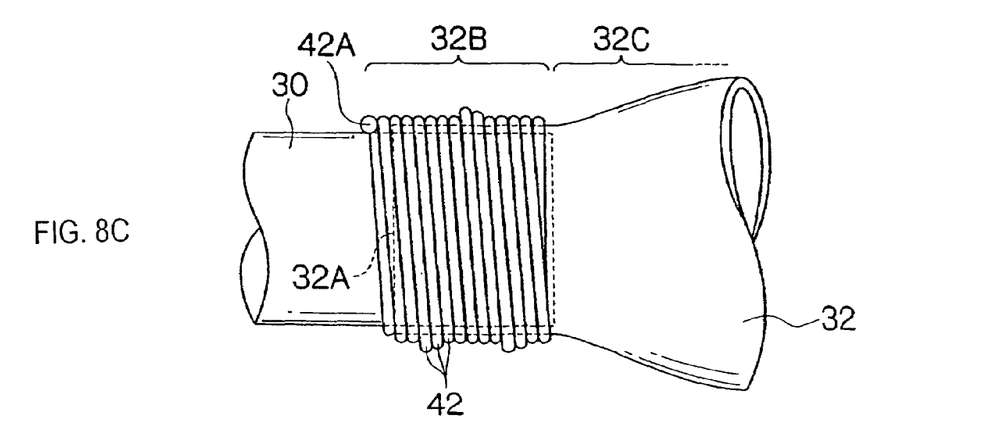

As shown in FIG. 8C, after the thread 42 is wound densely around the fixed part 32B, the both ends of the thread 42 are tied together outside the edge 32A (i.e., on the mounting ring 30). Since the knot 42A of the thread 42 is disposed outside the edge 32A of the balloon 32, it is possible to dispose the knot 42A lower than the winding part of the thread 42 so as to prevent the knot 42A from protruding. More specifically, since the both ends of the thread 42 is disposed on the edge 32A side when the thread 42 is tied together, it is possible to tie them together firmly without allowing the thread 42 to slacken.

Furthermore, according to another embodiment, since the thread 42 is tied on the edge 32A side (i.e., opposite to the expanded area 32C), it is possible to prevent the expanded area 32C from being damaged when the thread 42 is tied. Moreover, since the knot 42A of the thread 42 is disposed opposite to the expanded area 32C, it is possible to prevent the balloon 32 from being damaged by the knot 42A when the expanded area 32C is expanded or shrunken. The method of tying the ends of the thread 42 together is not limited to tying the ends of the thread 42 together, but the ends of the thread 42 may be bonded using an adhesive, for example.

According to another embodiment, since the thread 42 is tied outside the edge 32A of the balloon 32, it is possible to prevent the knot 42A from protruding when the thread 42 is tied on the balloon 32. Therefore, when the ultrasonograph is passed through the clamp channel of an endoscope, it is possible to insert the ultrasonograph smoothly and prevent the balloon 32 from being damaged.

In the above-described embodiment, though the thread 42 is tied outside the edge 32A of the balloon 32, it is preferable to tie the thread 42 at the outside area of the balloon 32.

Figure 9A:
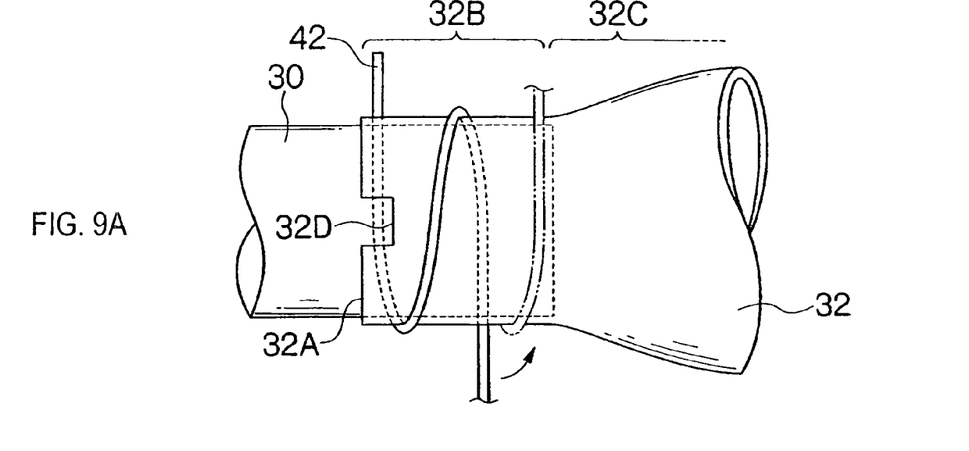
FIGS. 9A to 9C are perspective side views showing a fixing method of another embodiment different from FIG. 8.
Figure 9B:
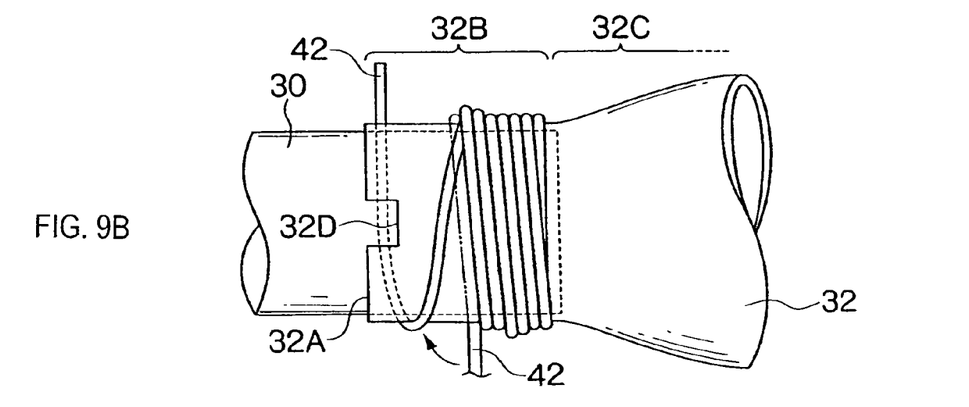
Figure 9C:
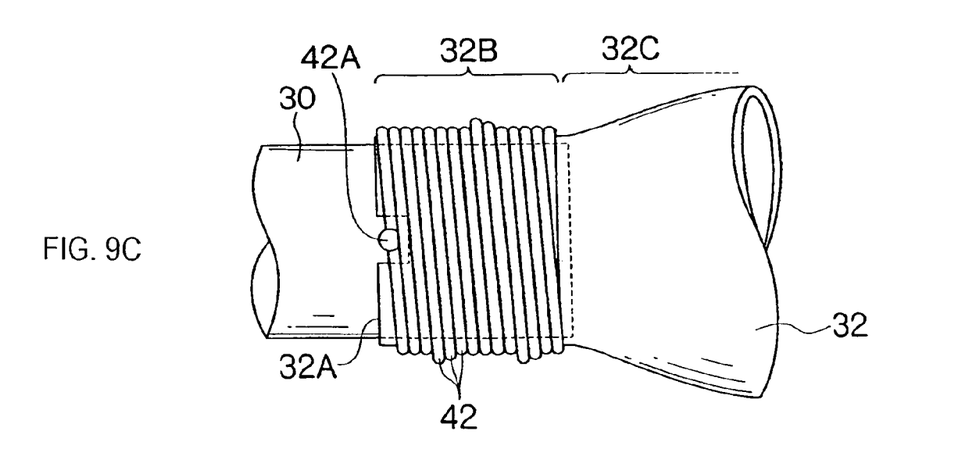

Therefore, as shown in FIGS. 9A to 9C, it is also possible to form a notch 32D at the edge 32A of the balloon 32 and tie the thread 42 at this notch 32D. First, as shown in FIG. 9A, the thread 42 is wound roughly around the fixed part 32B after the thread 42 is wound from the edge 32A of the balloon 32. Next, as shown in FIG. 9B, the thread 42 is wound densely toward the edge 32A. Then, as shown in FIG. 9C, the ends of the thread 42 are tied together after the knot 42A of the thread 42 is disposed at the notch 32D. Therefore, since the knot 42A is disposed on the mounting ring 30, it is possible to prevent the knot 42A from protruding.

Next, a further embodiment of the fixing method according to the present invention will be explained.

Figure 10A:
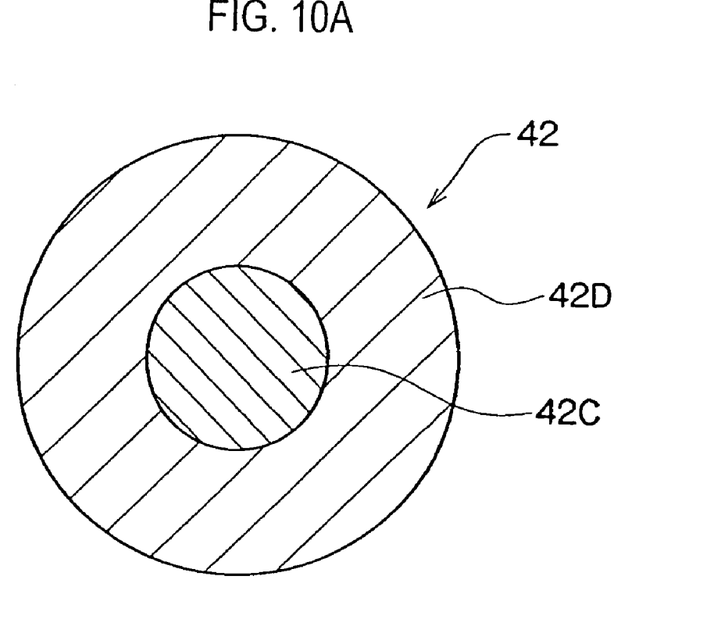
FIGS. 10A and 10B are sectional views of a thread used in further embodiment.
Figure 10B:
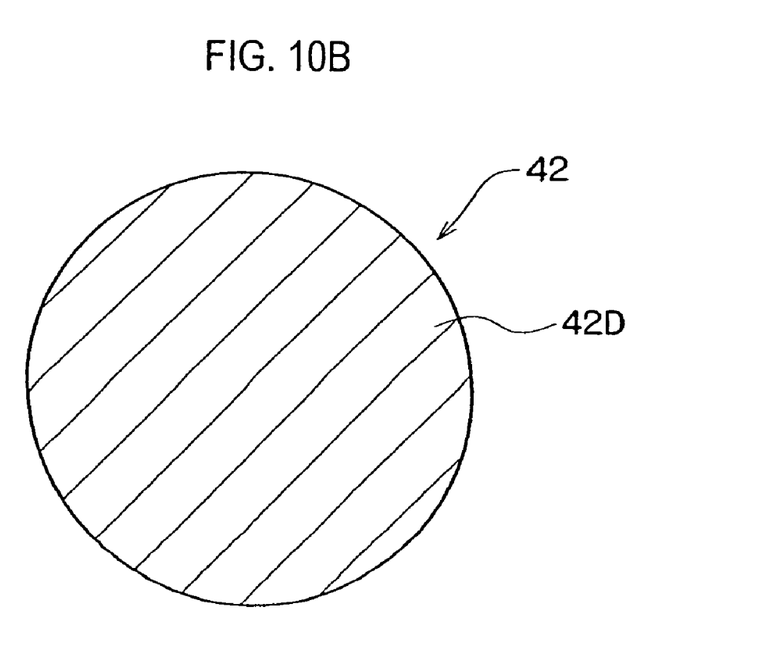

In this embodiment, at least the outer surface of the thread 42 is made of a molten material such as thermo-fusible resin. For example, a core material 42C of the thread 42 as shown in FIG. 10A is covered with a molten material 42D. The molten material 42D is a material that is melted by heating while completely solidified by cooling to approximately a normal temperature. As shown in FIG. 10B, it is also possible to constitute the entire thread 42 using the molten material 42D.

Figure 11A:
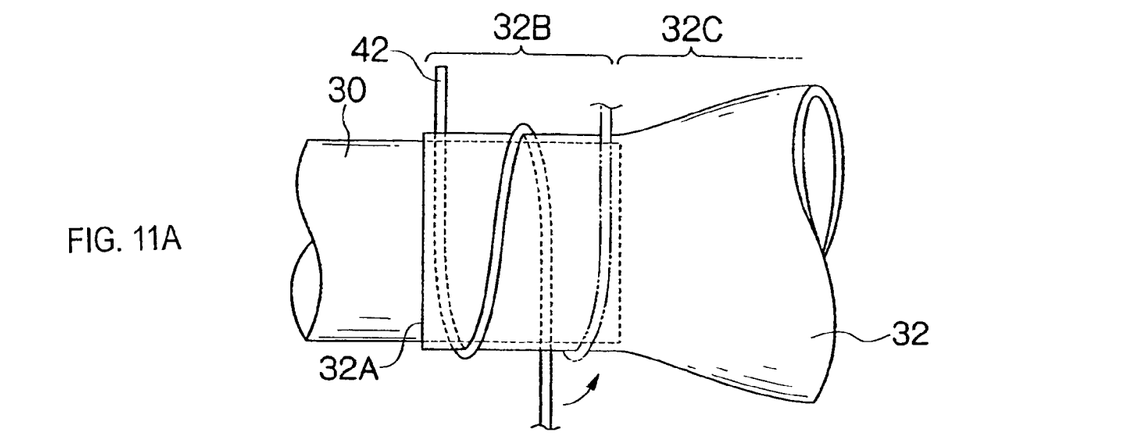
FIGS. 11A to 11C are perspective side views showing a fixing method using a thread in FIG. 10.
Figure 11B:
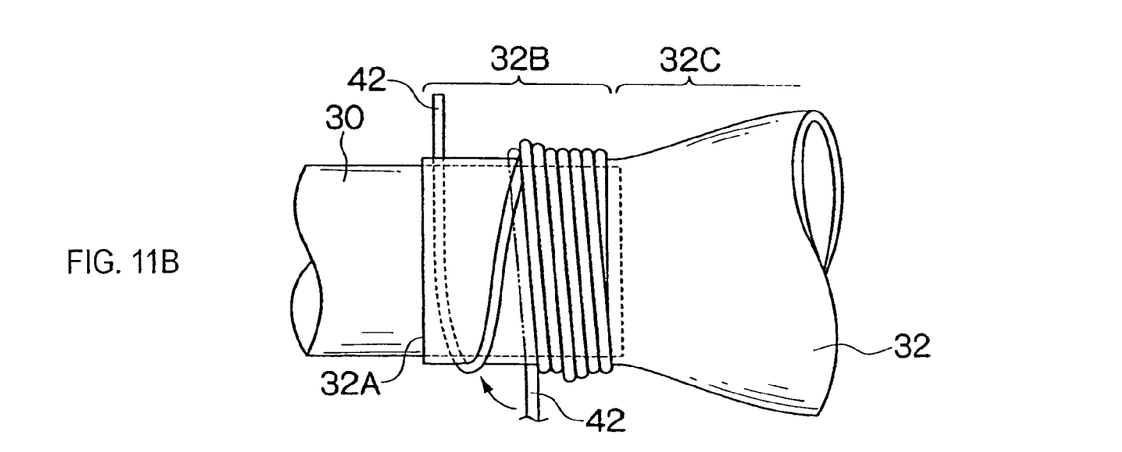
Figure 11C:
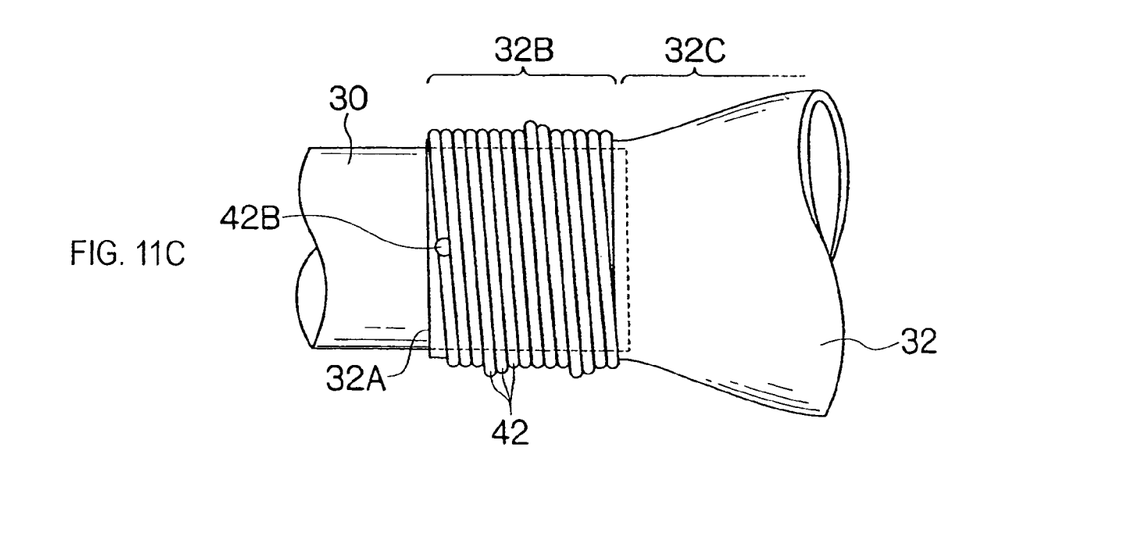

The balloon 32 is fixed using the above-described thread 42. First, as shown in FIG. 11A, the thread 42 is wound roughly from the edge 32A of the balloon 32. Next, as shown in FIG. 11B, the thread 42 is wound densely toward the edge 32A. Then, after the ends of the thread 42 are tied together, the tied part is spot-heated using a soldering iron and the like. Therefore, as shown in FIG. 11C, a fused part 42B is formed by fusing the both ends of the thread 42. Since the fused part 42B is formed by fusing and solidifying fusible resin, it is possible to prevent the fused part 42B from protruding. Furthermore, according to the further embodiment, since the ends of the thread 42 are fused together, it is possible to attach the both ends of the thread 42 together without forming any protrusion. In addition, since only the ends of the thread 42 are spot-fused, in the case where the entire thread 42 is fused, it is possible to prevent the thread 42 from slackening and to fix the balloon 32 firmly.

In the above-described embodiment, the ends of the thread 42 are tied together on the edge 32A side of the balloon 32, but the present invention is not limited to those. The ends of the thread 42 may also be tied together on the expanded area 32C side of the balloon 32.

Furthermore, in the above-described second embodiment, the ends of the thread 42 are fused on the balloon 32, but the present invention is not limited to those. disposing the fused part 42B outside the balloon 32 (i.e., on the mounting ring 30) can reliably prevent the fused part 42B from protruding.

Additionally, the molten material which is melted by heating is used in the above-described further embodiment, but it is also possible to use a material such as resin or rubber which has the bonding effect by being dissolved by a solvent instead of the molten material.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A method for fixing one of a balloon and a tubular member to an object with a thread for a medical apparatus, comprising:
    covering the object with an end of the one of the balloon and the tubular member;
    winding the thread at a first pitch in a first direction from an edge of the end of the one of the balloon and the tubular member toward an intermediate position of the one of the balloon and the tubular member; and
    winding the thread at a second pitch in a second direction opposite to the first direction, the second pitch being shorter than the first pitch.

2. The method for fixing one of a balloon and a tubular member as defined in claim 1, wherein the object is one of an insertion section of an endoscope, an insertion adapter covered over the insertion section for assisting in inserting the insertion section, and an endoscope operating equipment for inserting through a clamp channel of the endoscope.

3. The method for fixing one of a balloon and a tubular member as defined in claim 1 further including knotting both ends of the thread on the object.

4. The method for fixing one of a balloon and a tubular member as defined in claim 3, wherein the object is one of an insertion section of an endoscope, an insertion adapter covered over the insertion section for assisting in inserting the insertion section, and an endoscope operating equipment for inserting through a clamp channel of the endoscope.

5. The method for fixing one of a balloon and a tubular member as defined in claim 1, further including fusing both ends of the thread.

6. The method for fixing one of a balloon and a tubular member as defined in claim 5, wherein the both ends of the thread is fused on the object.

7. The method for fixing one of a balloon and a tubular member as defined in claim 6, wherein the object is one of an insertion section of an endoscope, an insertion adapter covered over the insertion section for assisting in inserting the insertion section, and an endoscope operating equipment for inserting through a clamp channel of the endoscope.

8. The method for fixing one of a balloon and a tubular member as defined in claim 5, wherein the object is one of an insertion section of an endoscope, an insertion adapter covered over the insertion section for assisting in inserting the insertion section, and an endoscope operating equipment for inserting through a clamp channel of the endoscope.

9. The method for fixing one of a balloon and a tubular member as defined in claim 1, wherein the first pitch is about three times the diameter of the thread.

10. The method for fixing one of a balloon and a tubular member as defined in claim 1, wherein the thread windings of the second pitch contact one another.

11. The method for fixing one of a balloon and a tubular member as defined in claim 1, wherein the thread windings of the second pitch overlap the thread windings of the first pitch.

12. A medical apparatus, comprising:
    an endoscope insertion section having a clamp channel;
    an insertion adapter for assisting in inserting the endoscope insertion section;
    a long-length medical operating equipment inserted through the clamp channel or directly into a body cavity; and
    one of a balloon and a tubular member fixed with a thread to the medical operating equipment, wherein:
        the thread is wound at a first pitch in a first direction from an edge of the end of the one of the balloon and the tubular member toward an intermediate position of the one of the balloon and the tubular member; and
        then the thread is wound at a second pitch in a second direction opposite to the first direction, the second pitch being shorter than the first pitch.

13. The medical apparatus as defined in claim 12, wherein: both ends of the thread are knotted on the insertion section end of one of the balloon and the tubular member.

14. The medical apparatus as defined in claim 13, wherein the both ends of the thread are fused.

15. The method for fixing one of a balloon and a tubular member as defined in claim 12, wherein the first pitch is about three times the diameter of the thread.

16. The method for fixing one of a balloon and a tubular member as defined in claim 12, wherein the thread windings of the second pitch contact one another.

17. The method for fixing one of a balloon and a tubular member as defined in claim 12, wherein the thread windings of the second pitch overlap the thread windings of the first pitch.

* * * * *